(12) United States Patent
Matsubara et al.

(10) Patent No.: US 10,053,435 B2
(45) Date of Patent: Aug. 21, 2018

(54) FUROXAN COMPOUND, AND MANUFACTURING METHOD FOR SAME

(71) Applicant: NATIONAL UNIVERSITY CORPORATION KOBE UNIVERSITY, Kobe-shi, Hyogo (JP)

(72) Inventors: Ryosuke Matsubara, Hyogo (JP); Akihiro Ando, Hyogo (JP); Masahiko Hayashi, Hyogo (JP)

(73) Assignee: NATIONAL UNIVERSITY CORPORATION KOBE UNIVERSITY, Kobe-shi, Hyogo (JP)

( * ) Notice: Subject to any disclaimer, the term of this patent is extended or adjusted under 35 U.S.C. 154(b) by 0 days.

(21) Appl. No.: 15/543,547

(22) PCT Filed: Dec. 15, 2015

(86) PCT No.: PCT/JP2015/006260
§ 371 (c)(1),
(2) Date: Jul. 13, 2017

(87) PCT Pub. No.: WO2016/113802
PCT Pub. Date: Jul. 21, 2016

(65) Prior Publication Data
US 2018/0009771 A1 Jan. 11, 2018

(30) Foreign Application Priority Data
Jan. 14, 2015 (JP) .................... 2015-004700

(51) Int. Cl.
C07D 271/08 (2006.01)
(52) U.S. Cl.
CPC .................. C07D 271/08 (2013.01)
(58) Field of Classification Search
CPC .................................. C07D 271/08
See application file for complete search history.

(56) References Cited

FOREIGN PATENT DOCUMENTS

| CN | 101812015 A | 8/2010 |
| JP | 11240874 A | 9/1999 |
| WO | 9401422 A1 | 1/1994 |

OTHER PUBLICATIONS

Dorwald, F. Zaragoza. Side Reactions in Organic Synthesis: A Guide to Successful Synthesis Design, Weinheim: Wiley-VCH Verlag GmbH & Co. KGaA, 2005, Preface (Year: 2005).*
Kunai et al. Bull. Chem. Soc. Jpn. 1990, 63, 1843-1844 (Year: 1990).*
Sheremetev et al. Mendeleev Commun. 2006, 16, 163-165 (Year: 2006).*
Clark J. et al., "Fluorodenitrations Using Tetrabutylammonium Fluoride", Tetrahedron Letters, vol. 26, No. 18, 1985, pp. 2233-2236.
Andrianov, V. G. et al., "Influence of Substituents on the Relative Stability of Furoxan Isomers", Khimia Geterocikicheskih Soedinenii, 1986, No. 2, pp. 264-266. (See Non-Patent Literature Document 9, International Search Report Issued in PCT Application PCT/JP2015/006260, for Explanation of Relevance).
Ferioli R. et al., "A New Class of Furoxan Derivatives as NO Donors: Mechanism of Action and Biological Activity", British Journal of Pharmacology, vol. 114, No. 4, Feb. 1995, pp. 816-820.
Kuduk S. et al., "Tetrabutylammonium Salt Induced Denitration of Nitropyridines: Synthesis of Fluoro-, Hydroxy-, and Methoxypyridines", Organic Letters, vol. 7, No. 4, Jan. 22, 2005, pp. 577-579.
Cena C. et al., "Use of the Furoxan (1, 2, 5-oxadiazole 2-oxide) System in the Design of New NO-donor Antioxidant Hybrids" ARKIVOC, Jan. 27, 2006, pp. 301-309.
Pasinszki T. et al., "Dimerisation of Nitrile Oxides: a Quantum-Chemical Study" Phsyical Chemistry Chemical Physics, 11, Apr. 17, 2009, pp. 5263-5272.
Serafim R.A.M. et al., "Nitric Oxide: State of the Art in Drug Design", Current Medicinal Chemistry, vol. 19, No. 3, Jan. 2012, pp. 386-405.
Tang W. et al., "Novel Nitric Oxide-Releasing Derivatives of Brusatol as Anti-Inflammatory Agents: Design, Synthesis, Biological Evaluation, and Nitric Oxide Release Studies", Journal of Medicinal Chemistry, vol. 57, No. 18, Sep. 2, 2014, pp. 7600-7612.
ISA Japan Patent Office, International Search Report Issued in PCT Application No. PCT/JP2015/006260, dated Mar. 8, 2016, WIPO, 2 pages.
Gasco, et al., "The NO-Releasing Heterocycles," Nitric Oxide Donors: for Pharmaceutical and Biological Applications, John Wiley & Sons Inc., 2005, pp. 131-134.

* cited by examiner

*Primary Examiner* — Matthew P Coughlin
(74) *Attorney, Agent, or Firm* — Alleman, Hall, Creasman & Tuttle, LLP

(57) ABSTRACT

The present invention provides: a furoxan compound having a fluorine atom as a substituent group on the ring structure thereof; and a novel nitric oxide donor including the compound. The present invention relates to a fluorofuroxan compound represented by general formula (1) or (2). The compound of formula (1) can be manufactured by reacting a fluoride salt with a nitrofuroxan compound to substitute the nitro group with a fluoro group. The compound of formula (2) can be manufactured by subjecting the compounds of formula (1) to isomerization by irradiation with light.

[Chemical Formula 1]

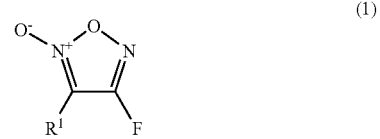

(1)

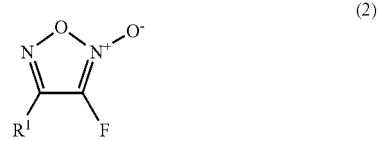

(2)

6 Claims, No Drawings

FUROXAN COMPOUND, AND MANUFACTURING METHOD FOR SAME

TECHNICAL FIELD

The present invention relates to a novel furoxan compound and a method for manufacturing the same.

BACKGROUND ART

Nitric oxide is one of neurotransmitters and is known to have vasodilatory action and memory enhancing action. For this reason, nitric oxide has been studied to apply to a drug for treating epilepsy or Alzheimer type dementia. Nitric oxide is also a central substance of action mechanism of nitroglycerin as a drug for angina pectoris and VIAGRA as a drug for erectile dysfunction.

In recent years, furoxan (1,2,5-oxadiazole-2-oxide) has attracted attention as a compound that releases nitric oxide under physiological conditions and is expected as a new medical lead compound (for example, see Non-Patent Literatures 1 and 2).

However, although the nitric oxide-releasing ability exhibited by the furoxan compound is largely dependent on the position and property of the substituent on the ring structure, only a limited number of methods for synthesizing the furoxan compound are known (see, for example, Patent Literature 1). Therefore, the types of substituents included in conventionally known furoxan compounds were limited.

CITATION LISTS

Patent Literature

PTL 1: JP 11-240874 A

Non-Patent Literatures

Non-Patent Literature 1: R. A. M. Serafim et al., Current Medicinal Chemistry, 2012, 19, pp. 386-405
Non-Patent Literature 2: Weibin Tang et al., J. Med. Chem., 2014, 57, pp. 7600-7612

SUMMARY OF INVENTION

Technical Problem

No furoxan compounds having a fluorine atom as a substituent on the ring structure have been reported so far.

An object of the present invention is to provide a furoxan compound having a fluorine atom as a substituent on the ring structure thereof, as well as to provide a novel nitric oxide donor including the compound.

Solution to Problem

The present inventors have studied to synthesize a furoxan compound having a fluorine atom, and, as a result, succeeded in synthesizing a furoxan compound having a fluorine atom at the 4-position of the furoxan ring in one step using a readily available furoxan compound as a starting material. In addition, a furoxan compound having a fluorine atom at the 3-position has also been successfully synthesized by isomerizing the synthesized furoxan compound having a fluorine atom at the 4-position. Furthermore, when the synthesized furoxan compounds are evaluated for their ability to release nitric oxide, it has been found that both compounds can be used as a nitric oxide donor and the present invention has been completed based on these findings.

That is, the present invention relates to a fluorofuroxan compound represented by general formula (1) or (2) below.

[Chemical Formula 1]

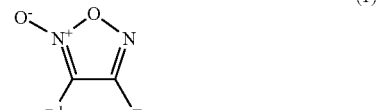

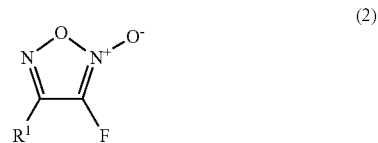

In each formula, $R^1$ represents hydrogen, halogen, a hydroxyl group, an alkyl group having 1 to 30 carbon atoms, an alkenyl group having 2 to 30 carbon atoms, an alkynyl group having 2 to 30 carbon atoms, an aryl group having 4 to 30 carbon atoms, an alkoxy group having 1 to 30 carbon atoms, an alkenyloxy group having 2 to 30 carbon atoms, an alkynyloxy group having 2 to 30 carbon atoms, an aryloxy group having 4 to 30 carbon atoms, an alkylsulfonyl group having 1 to 30 carbon atoms, an alkenylsulfonyl group having 2 to 30 carbon atoms, an alkynylsulfonyl group having 2 to 30 carbon atoms, an arylsulfonyl group having 4 to 30 carbon atoms, an acyl group having 1 to 30 carbon atoms, an alkoxycarbonyl group having 1 to 30 carbon atoms, an aryloxycarbonyl group having 4 to 30 carbon atoms, a thiocarbonyl group, a carboxyl group, an amino group, a monoalkylamino group having 1 to 30 carbon atoms, a dialkylamino group having 2 to 30 carbon atoms, a monoarylamino group having 4 to 30 carbon atoms, a diarylamino group having 8 to 30 carbon atoms, a carbonylamino group, a sulfonylamino group, a cyano group, a nitro group, an alkylsulfinyl group having 1 to 30 carbon atoms, an arylsulfinyl group having 4 to 30 carbon atoms, an alkylthio group having 1 to 30 carbon atoms, an arylthio group having 4 to 30 carbon atoms, a phosphoryl group, a dialkylaminocarbonyl group having 2 to 30 carbon atoms, or a monoalkylaminocarbonyl group having 1 to 30 carbon atoms.

Also, the present invention relates to a nitric oxide donor comprising the fluorofuroxan compound.

The present invention further relates to a method for manufacturing a fluorofuroxan compound represented by general formula (1), the method including a step of reacting a nitrofuroxan compound represented by general formula (3) below with a fluoride salt to substitute a nitro group with a fluoro group.

[Chemical Formula 2]

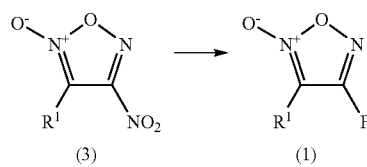

In the formula, $R^1$ is the same as $R^1$ described above.

The present invention still further relates to a method for manufacturing a fluorofuroxan compound represented by general formula (2), the method including a step of isomerizing the fluorofuroxan compound represented by general formula (1) by irradiation with light.

[Chemical Formula 3]

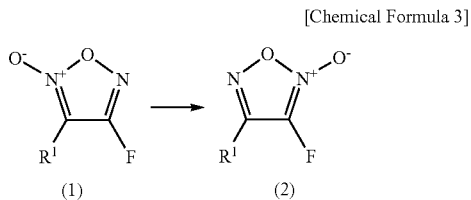

In the formula, $R^1$ is the same as $R^1$ described above.

Advantageous Effect of Invention

According to the present invention, it is possible to provide a novel furoxan compound having a fluorine atom introduced at the 3- or 4-position of the furoxan ring.

A furoxan compound having a fluorine atom at the 4-position can be synthesized in one step using a readily available furoxan compound as a starting material. Further, a furoxan compound having a fluorine atom at the 3-position can be easily synthesized by irradiating a furoxan compound having a fluorine atom at the 4-position with light.

These furoxan compounds having a fluorine atom can be suitably used, for example, as a nitric oxide donor capable of releasing nitric oxide under physiological conditions.

In addition, since the furoxan compound having a fluorine atom can be easily converted to a furoxan compound having a carbon-based substituent, such a furoxan compound can serve as a starting material for synthesizing furoxan compounds having various substituents.

DESCRIPTION OF EMBODIMENTS

Hereinafter, the present invention will be described in detail.

(Fluorofuroxan Compound)

The fluorofuroxan compound of the present invention is a compound represented by the following general formula (1) or (2). The fluorofuroxan compound of general formula (1) has a fluorine atom at the 4-position of the furoxan ring, and the fluorofuroxan compound of general formula (2) has a fluorine atom at the 3-position of the furoxan ring.

In the general formulas (1) and (2), $R^1$ is not particularly limited, but examples of $R^1$ include hydrogen, halogen, a hydroxyl group, an alkyl group having 1 to 30 carbon atoms, an alkenyl group having 2 to 30 carbon atoms, an alkynyl group having 2 to 30 carbon atoms, an aryl group having 6 to 30 carbon atoms, an alkoxy group having 1 to 30 carbon atoms, an alkenyloxy group having 2 to 30 carbon atoms, an alkynyloxy group having 2 to 30 carbon atoms, an aryloxy group having 6 to 30 carbon atoms, an alkylsulfonyl group having 1 to 30 carbon atoms, an alkenylsulfonyl group having 2 to 30 carbon atoms, an alkynylsulfonyl group having 2 to 30 carbon atoms, an arylsulfonyl group having 6 to 30 carbon atoms, an acyl group having 1 to 30 carbon atoms, an alkoxycarbonyl group having 1 to 30 carbon atoms, an aryloxycarbonyl group having 4 to 30 carbon atoms, a thiocarbonyl group, a carboxyl group, an amino group, a monoalkylamino group having 1 to 30 carbon atoms, a dialkylamino group having 2 to 30 carbon atoms, a monoarylamino group having 4 to 30 carbon atoms, a diarylamino group having 8 to 30 carbon atoms, a carbonylamino group, a sulfonylamino group, a cyano group, a nitro group, an alkylsulfinyl group having 1 to 30 carbon atoms, an arylsulfinyl group having 4 to 30 carbon atoms, an alkylthio group having 1 to 30 carbon atoms, an arylthio group having 4 to 30 carbon atoms, a phosphoryl group, a dialkylaminocarbonyl group having 2 to 30 carbon atoms, and a monoalkylaminocarbonyl group having 1 to 30 carbon atoms.

Although the upper limit of the number of carbon atoms in $R^1$ is set to 30 or less in each case, such an upper limit is preferably 20 or less, more preferably 10 or less.

Examples of alkyl in the alkyl group, alkyloxy group, alkylsulfonyl group and the like include methyl, ethyl, propyl, butyl, pentyl, hexyl, heptyl, octyl, and the like. Similarly, examples of alkenyl include ethenyl, propenyl, butenyl, and the like. Examples of alkynyl include ethynyl, propynyl, butynyl, and the like. Examples of aryl include phenyl, benzyl, tolyl, xylyl, and the like. In addition, any of alkyl, alkenyl, and alkynyl may be linear, branched, or cyclic.

(Method for Synthesizing 4-Fluorofuroxan Compound)

The 4-fluorofuroxan compound represented by general formula (1) can be synthesized by reacting a 4-nitrofuroxan compound represented by general formula (3) with a fluoride salt as shown in the following reaction formula, and substituting the nitro group with a fluoro group.

[Chemical Formula 4]

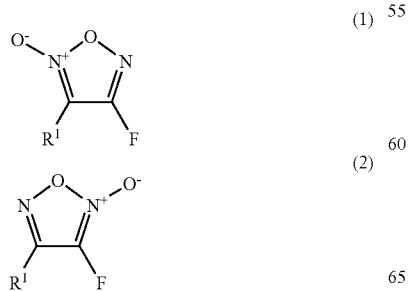

[Chemical Formula 5]

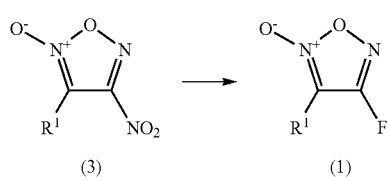

The 4-nitrofuroxan compound of general formula (3), which is the starting compound, is a furoxan compound having a nitro group at the 4-position of the furoxan ring, and has the same substituent $R^1$ at the 3-position as in general formula (1). The 4-nitrofuroxan compound is a known compound, and its synthesis method has been already known. For example, synthesis of 3-aryl-4-nitrofuroxan is disclosed in Kunai, A.; Doi, T.; Nagaoka, T.; Yagi, H.; Sasaki, K. Bull. Chem. Soc. Jpn. 1990, 63, 1843-1844.

Synthesis of 3-alkyl-4-nitrofuroxan is disclosed in Feng, C. Loh, T.-P. Angew. Chem. Int. Ed. 2013, 52, 12414-12417 and Fershtat, L. L.; Struchkova, M. I.; Goloveshkin, A. S.; Bushmarinov, I. S.; Makhova, N. N. Heteroatom Chem. 2014, 25, 226-237.

The 4-fluorofuroxan compound of general formula (1) is synthesized by substituting the nitro group at the 4-position of the 4-nitrofuroxan compound of general formula (3) with a fluoro group. In this substitution reaction, a fluoride salt is used as a reaction reagent.

The fluoride salt is not particularly limited so long as the nitro group of the nitrofuroxan compound of general formula (3) can be substituted with a fluoro group, and specific examples thereof include tetraalkylammonium fluorides such as tetrabutylammonium fluoride, alkali metal fluorides such as potassium fluoride and cesium fluoride, and the like. The amount of the fluoride salt to be used is not particularly limited and may be equal to or more than the number of moles used for the 4-nitrofuroxan compound of general formula (3).

When an alkali metal fluoride is used as the fluoride salt, it is preferable to use a tetraalkylammonium fluoride or a tetraalkylphosphonium fluoride as a catalyst. Since these catalysts have a high lipophilic property and are soluble in an organic solvent, the reactivity of the alkali metal fluoride to the 4-fluorofuroxan compound can be increased.

The solvent used in this substitution reaction is not particularly limited, and examples thereof can include general solvents such as tetrahydrofuran, dimethylformamide, dichloromethane, dichloroethane, chloroform, carbon tetrachloride, pentane, hexane, heptane, benzene, toluene, xylene, acetonitrile, diethyl ether, cyclopentyl methyl ether, tertiary butyl methyl ether, acetic acid, methyl acetate, ethyl acetate, propyl acetate, butyl acetate, dimethyl sulfoxide, 1,4-dioxane, and the like.

The reaction temperature and the reaction time in the substitution reaction may be appropriately determined in consideration of, for example, the type and reactivity of the 4-nitrofuroxan compound or the fluoride salt, and the reaction can proceed at a relatively mild temperature such as −78° C. to 100° C., preferably −20° C. to 80° C., over a period of about 10 minutes to 24 hours.

By this substitution reaction, the 4-fluorofuroxan compound represented by general formula (1) can be synthesized in a high yield (for example, in a yield of 80 to 100%).

Incidentally, the present inventors have found that, in place of the fluoride salt, when a chloride salt (e.g., a tetraalkylammonium chloride or an alkali metal chloride) or a cyanide salt (e.g., a tetraalkylammonium cyanide or an alkali metal cyanide) is reacted with the 4-nitrofuroxan compound represented by general formula (3), the nitro group of the 4-nitrofuroxan compound is converted into a chloro group or a cyano group to synthesize a furoxan compound having a chloro group or a cyano group at the 4-position. Specific examples of these reactions are shown in Reference Example 1 and Reference Example 2 described later.

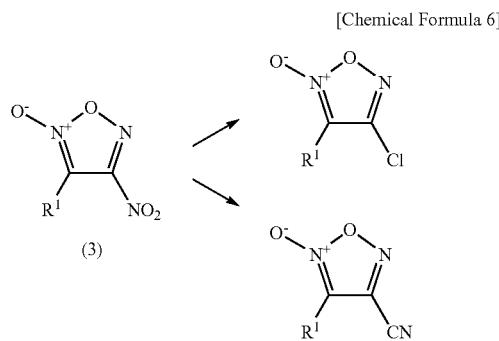

[Chemical Formula 6]

(Method for Synthesizing 3-Fluorofuroxan Compound)

When the 4-fluorofuroxan compound of general formula (1) described above is irradiated with light, the compound is isomerized to give a 3-fluorofuroxan compound represented by general formula (2).

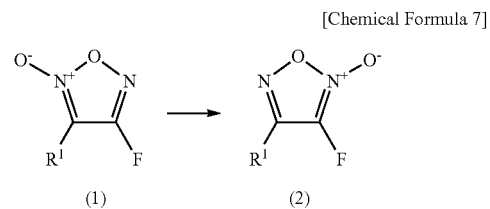

[Chemical Formula 7]

The wavelength and irradiation time of the light to be used are not particularly limited, and the wavelength and time necessary for the isomerization may be appropriately set. As a specific example, the wavelength can be 260 to 600 nm and the time can be 1 to 24 hours.

In the isomerization, it is preferable to irradiate the 4-fluorofuroxan compound of general formula (1) with light in a state of being dissolved in a solvent as appropriate. The temperature conditions for the isomerization are not particularly limited, but, for example, the temperature may be about −78 to 80° C.

By the isomerization with light irradiation, the 3-fluorofuroxan compound of general formula (2) can be synthesized in a high yield.

(Nitric Oxide Donor)

The fluorofuroxan compound of the invention, represented by general formula (1) or (2), can be used as an extremely excellent nitric oxide donor.

In detail, since the 3-fluorofuroxan compound of general formula (2) itself can have a very high nitric oxide-releasing ability, such a compound can be a powerful nitric oxide donor. On the other hand, the 4-fluorofuroxan compound of general formula (1) itself exhibits almost no nitric oxide-releasing ability, but as described above, when irradiated with light, the 4-fluorofuroxan compound can be isomerized to the 3-fluorofuroxan compound of general formula (2) having an extremely high nitric oxide-releasing ability. Thus, the 4-fluorofuroxan compound of general formula (1) can be used as a light stimulus-responsive nitric oxide donor, which acquires the ability to release nitric oxide upon irradiation with light.

(Reaction Example Utilizing Fluorofuroxan Compound of the Invention)

The fluorofuroxan compound of the present invention, represented by general formula (1) or (2), is a very useful compound because furoxan compounds having various substituents can be synthesized using the fluorofuroxan compound as a starting compound. That is, by converting the fluorine atom of the fluorofuroxan compound represented by general formula (1) or (2) into various substituents, furoxan compound having various substituents can be easily synthesized.

As a specific example, by reacting the fluorofuroxan compound of general formula (1) or (2) with a silicon compound having a specific substituent $R^2$, the fluorine atom on the furoxan ring is substituted with a specific substituent $R^2$, thereby to be able to obtain a furoxan compound having a specific substituent $R^2$.

[Chemical Formula 8]

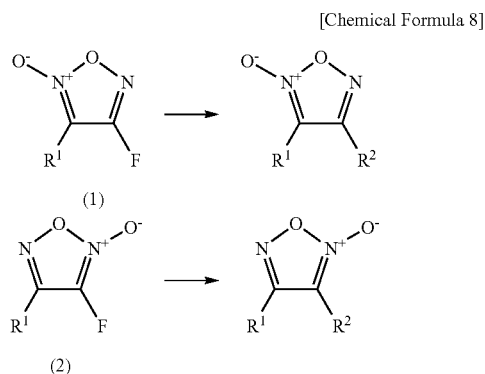

Examples of the specific substituent $R^2$ include a cyano group, an alkylethynyl group, an arylethynyl group, a perfluoroalkyl group (e.g., trifluoromethyl group, etc.), a perfluoroaryl group, an allyl group, a triarylmethyl group, and the like. Examples of the silicon compound having the specific substituent $R^2$ include a silane having a specific substituent $R^2$ and a trialkyl group, and the like. The amount used of the silicon compound having the specific sub stituent $R^2$ is not particularly limited and may be equal to or more than the number of moles of the fluorofuroxan compound used.

In this reaction, it is preferable to use the above-mentioned tetraalkylammonium fluoride or tetraalkylphosphonium fluoride as a catalyst.

The solvent used in this substitution reaction is not particularly limited, and examples thereof can include general solvents such as tetrahydrofuran, dimethylformamide, dichloromethane, dichloroethane, chloroform, carbon tetrachloride, pentane, hexane, heptane, benzene, toluene, xylene, acetonitrile, diethyl ether, cyclopentyl methyl ether, tertiary butyl methyl ether, acetic acid, methyl acetate, ethyl acetate, propyl acetate, butyl acetate, dimethyl sulfoxide, 1,4-dioxane, and the like.

The reaction temperature and the reaction time in the substitution reaction may be appropriately determined in consideration of, for example, the type and reactivity of the fluorofuroxan compound or the silicon compound, and the reaction may be allowed to proceed at a relatively mild temperature such as −78° C. to 100° C., preferably −20° C. to 80° C., over a period of about 1 to 24 hours. Specific examples of these reactions are shown in Reference Examples 3 to 5 described later.

In this way, it is possible to synthesize furoxan compounds having a wide variety of carbon-based substituents using the fluorofuroxan compound of the present invention as a starting compound. As a result, it is expected that it will be possible to promptly advance development of medicals for conditions involving nitric oxide, such as epilepsy, Alzheimer type dementia, and heart disease.

EXAMPLES

Hereinafter, the present invention will be described in more detail by way of examples, but is not limited to these examples.

(Example 1) Synthesis of 4-Fluorofuroxan Compound

[Chemical Formula 9]

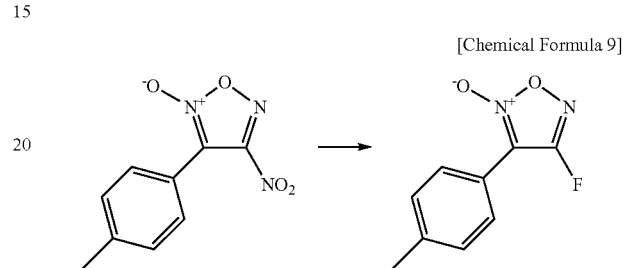

3-(4-Methylphenyl)-4-nitrofuroxan (500 mg) was dissolved in tetrahydrofuran (4.6 mL) and the resulting solution was cooled to 0° C. A solution of tetrabutylammonium fluoride in tetrahydrofuran (1 M, 2.9 mL) was slowly added dropwise to the resulting solution. After stirring the mixture at 0° C. for 1 hour, a saturated aqueous ammonium chloride solution was added thereto and the mixture was extracted with methylene chloride. After drying the extract over anhydrous sodium sulfate, the solid was removed by filtration and then the solvent was distilled off under reduced pressure. The obtained residue was purified by silica gel chromatography to obtain 404 mg (yield: 92%) of 4-fluoro-3-(4-methylphenyl)furoxan.

(Example 2) Synthesis of 4-Fluorofuroxan Compound

[Chemical Formula 10]

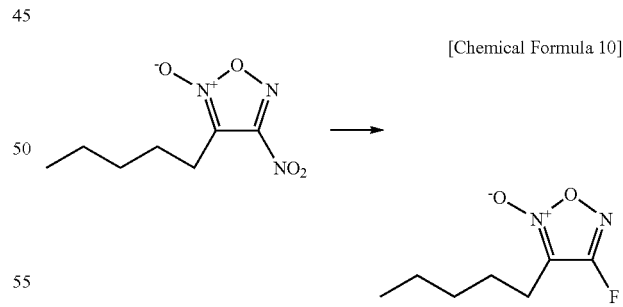

4-Nitro-3-pentylfuroxan (40.2 mg) was dissolved in tetrahydrofuran (0.5 mL) and the resulting solution was cooled to 0° C. A solution of tetrabutylammonium fluoride in tetrahydrofuran (1 M, 0.26 mL) was slowly added dropwise to the resulting solution. After stirring the mixture at 0° C. for 1 hour, a saturated aqueous ammonium chloride solution was added thereto and the mixture was extracted with methylene chloride. After drying the extract over anhydrous sodium sulfate, the solid was removed by filtration and then the solvent was distilled off under reduced pressure. The obtained residue was purified by silica gel chromatography to obtain 31.3 mg (90% yield) of 4-fluoro-3-pentylfuroxan.

(Reference Example 1) Synthesis of 4-Chlorofuroxan Compound and 3-Chlorofuroxan Compound

[Chemical Formula 11]

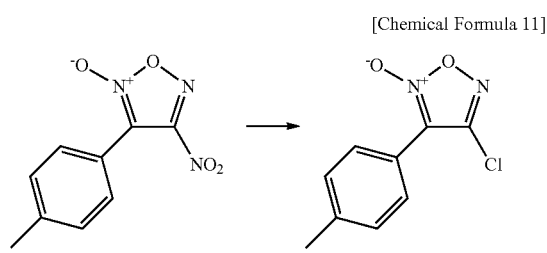

Tetrabutylammonium chloride (111.2 mg, 0.4 mmol) and 3-(4-methylphenyl)-4-nitrofuroxan (44.2 mg, 0.2 mmol) were weighed into a flask, and dimethylformamide (0.5 mL) was added. The reaction solution was sealed and stirred at 80° C. for 14 hours. The reaction solution was cooled to room temperature, and water (2 mL) and diethyl ether (2 mL) were added. The mixture was subjected to liquid separation and the aqueous layer was further extracted with diethyl ether three times. The combined organic layers were dried by adding anhydrous sodium sulfate. After filtration, the solvent was distilled off under reduced pressure, and the obtained residue was purified by silica gel chromatography to obtain 20.2 mg (48% yield) of 4-chloro-3-(4-methylphenyl)furoxan. At the same time, 1.7 mg (4% yield) of 3-chloro-4-(4-methylphenyl)furoxan was obtained.

(Reference Example 2) Synthesis of 4-Cyanofuroxan Compound

[Chemical Formula 12]

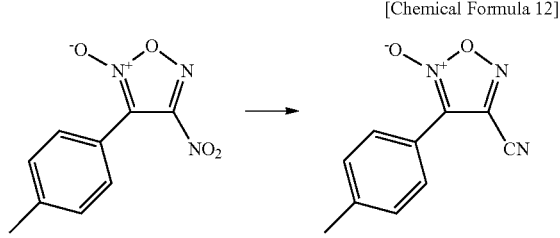

Tetrahydrofuran (0.75 mL) was added to tetrabutylammonium cyanide (105 mg), and then 3-(4-methylphenyl)-4-nitrofuroxan (66 mg) was added thereto at room temperature. After stirring the mixture for 30 minutes, the solvent was distilled off under reduced pressure. The obtained residue was purified by silica gel chromatography to obtain 54 mg (89% yield) of 4-cyano-3-(4-methylphenyl)furoxan.

(Example 3) Synthesis of 3-Fluorofuroxan Compound

[Chemical Formula 13]

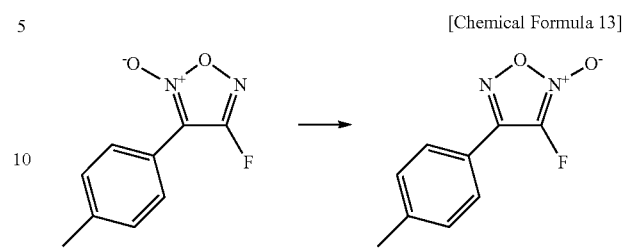

4-Fluoro-3-(4-methylphenyl)furoxan (51.7 mg, 0.23 mmol) was placed in a Pyrex (registered trademark) glass flask and 8 mL of benzene was added thereto. The mixture was degassed by ultrasonic wave for 1 minute while reducing the pressure to 50 mmHg. Under an argon atmosphere, the mixture was irradiated with light for 6 hours. Light having a wavelength of 300 to 400 nm was used. The solvent was distilled off under reduced pressure and the obtained residue was purified by silica gel chromatography to obtain 3-fluoro-4-(4-methylphenyl)furoxan (37.6 mg, 73% yield).

(Reference Example 3) Synthesis of 4-Cyanofuroxan Compound Using 4-Fluorofuroxan Compound as Starting Compound

[Chemical Formula 14]

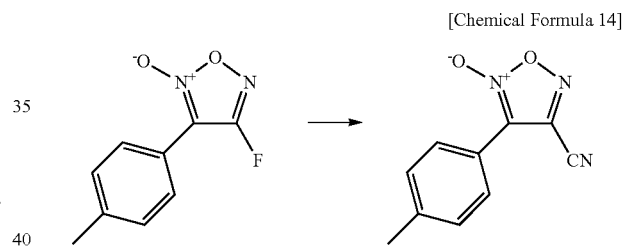

4-Fluoro-3-(4-methylphenyl)furoxan (38.8 mg) and trimethylsilyl cyanide (0.0325 mL) were dissolved in tetrahydrofuran (0.45 mL), and a solution of tetrabutylammonium fluoride in tetrahydrofuran (1 M, 0.04 mL) was slowly added dropwise thereto. After stirring the mixture for 1 hour, the solvent was distilled off under reduced pressure. The obtained residue was purified by silica gel chromatography to obtain 28.2 mg (70% yield) of 4-cyano-3-(4-methylphenyl)furoxan.

(Reference Example 4) Synthesis of 4-Trifluoromethylfuroxan Compound Using 4-Fluorofuroxan Compound as Starting Compound

[Chemical Formula 15]

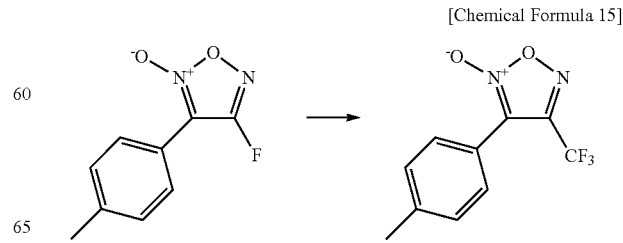

4-Fluoro-3-(4-methylphenyl)furoxan (38.8 mg) and trimethylsilyl trifluoromethane (0.089 mL) were dissolved in tetrahydrofuran (0.45 mL), and a solution of tetrabutylammonium fluoride in tetrahydrofuran (1 M, 0.01 mL) was slowly added dropwise thereto. After stirring the mixture for 1 hour, the solvent was distilled off under reduced pressure. The obtained residue was purified by silica gel chromatography to obtain 11.9 mg (16% yield) of 4-trifluoromethyl-3-(4-methylphenyl)furoxan.

(Reference Example 5) Synthesis of 4-(2-Phenylethynyl)Furoxan Compound Using 4-Fluorofuroxan Compound as Starting Compound

[Chemical Formula 16]

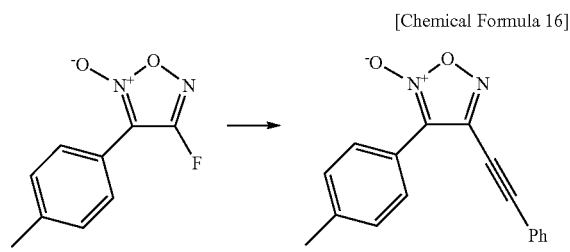

Tetrahydrofuran (0.25 mL) was added to 4-fluoro-3-(4-methylphenyl)furoxan (19.4 mg, 0.1 mmol). After addition of 1-phenyl-2-trimethylsilylacetylene (25.6 µL, 0.13 mmol) to the solution, a 1 M solution of tetrabutylammonium fluoride in tetrahydrofuran (20 µL, 0.02 mmol) was added thereto. After stirring the mixture at room temperature for 90 minutes, the solvent was distilled off under reduced pressure. The obtained residue was purified by silica gel chromatography to obtain 3-(4-methylphenyl)-4-(2-phenylethynyl)furoxan (17.3 mg, 63% yield).

Evaluation Example

The ability to release nitric oxide on each of (4-fluoro-3-(4-methylphenyl)furoxan, 3-fluoro-4-(4-methylphenyl)furoxan, 4-chloro-3-(4-methylphenyl)furoxan, and 3-chloro-4-(4-methylphenyl)furoxan was evaluated by the following method.

(Experimental Method)

Each furoxan compound and L-cysteine were dissolved in 50 mM phosphate buffer (pH 7.4) to have a concentration of 0.1 mM and 5 mM, respectively, thereby to prepare a solution with a total volume of 6 mL. After stirring the solution at 37° C. for 1 hour, 3 mL of the solution was added to a light absorption cell and 250 µL of Griess reagent was added. After being left to stand at room temperature for 10 minutes, the absorbance was measured. The nitric oxide-releasing rate was obtained from a calibration curve prepared in advance using a sodium nitrite solution.

(Experimental Results)

Table 1 shows the nitric oxide-releasing rate of each of the furoxan compounds when it is considered that one molecule of furoxan compound releases one molecule of nitric oxide.

TABLE 1

| Furoxan | Nitric oxide-releasing rate | 3 - X/4 - X$^a$ |
|---|---|---|
| 4-Fluoro compound (Example) | 2.5% | 14.7 times |
| 3-Fluoro compound (Example) | 36.8% | |
| 4-Chloro compound (Reference Example) | 4.2% | 4.0 times |
| 3-Chloro compound (Reference Example) | 16.7% | |

$^a$NO-releasing rate of 3-halofuroxan/NO-releasing rate of 4-halofuroxan

As shown in Table 1, the nitric oxide-releasing rate of the 3-fluorofuroxan compound reached 14.7 times that of the 4-fluorofuroxan compound, and it was also twice or more even when compared to that of the 3-chlorofuroxan compound. From this, the 3-fluorofuroxan compound is found to show an extremely high nitric oxide-releasing ability. That is, it was found that the 3-fluorofuroxan compound can be used as an extremely potent nitric oxide donor.

In contrast, it can be understood that the 4-fluorofuroxan compound per se shows almost no nitric oxide-releasing ability. However, as shown in Example 3, the 4-fluorofuroxan compound is isomerized to the 3-fluorofuroxan compound by irradiation with light. The 3-fluorofuroxan compound produced by irradiating the 4-fluorofuroxan compound with light shows a nitric oxide-releasing ability which is 10 times or higher than that of the 4-fluorofuroxan compound. Thus, by utilizing this property, the 4-fluorofuroxan compound can be used as a light stimulus-responsive nitric oxide donor that acquires a nitric oxide-releasing ability only after irradiation with light.

Such a light stimulus-responsive nitric oxide donor having a furoxan skeleton has not been reported so far, and the present inventors have created the donor for the first time.

Since the light stimulus-responsive nitric oxide donor releases nitric oxide only when irradiated with light and only where irradiated with light, use as a tool for physiological experiments (e.g., observation of physiological responses in cells by releasing nitric oxide only in specific parts of the cells) or application as a site-specific cancer therapeutic agent utilizing the cytotoxic action of nitric oxide can be expected.

The invention claimed is:

1. A fluorofuroxan compound represented by general formula (1) or (2) below:

[Chemical Formula 1]

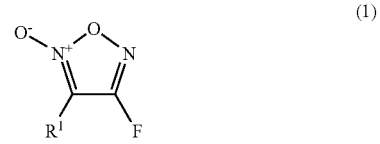

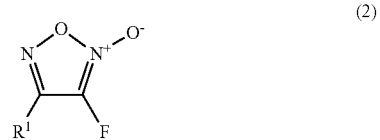

in each formula, $R^1$ represents a hydroxyl group, an alkyl group having 1 to 30 carbon atoms, an alkenyl group having 2 to 30 carbon atoms, an alkynyl group having 2 to 30 carbon atoms, an aryl group having 4 to 30 carbon atoms, an alkoxy group having 1 to 30 carbon atoms, an alkenyloxy group having 2 to 30 carbon atoms, an alkynyloxy group having 2 to 30 carbon atoms, an aryloxy group having 4 to 30 carbon atoms, an alkylsulfonyl group having 1 to 30 carbon atoms, an alkenylsulfonyl group having 2 to 30 carbon atoms, an alkynylsulfonyl group having 2 to 30 carbon atoms, an arylsulfonyl group having 4 to 30 carbon atoms, an acyl group having 1 to 30 carbon atoms, an alkoxycarbonyl group having 1 to 30 carbon atoms, an aryloxycarbonyl group having 4 to 30 carbon atoms, a thiocarbonyl group, a carboxyl group, an amino group, a monoalkylamino group having 1 to 30 carbon atoms, a dialkylamino group having 2 to 30 carbon atoms, a monoarylamino group having 4 to 30 carbon atoms, a diarylamino group having 8 to 30 carbon atoms, a carbonylamino group, a sulfonylamino group, a cyano group, a nitro group, an alkylsulfinyl group having 1 to 30 carbon atoms, an arylsulfinyl group having 4 to 30 carbon atoms, an alkylthio group having 1 to 30 carbon atoms, an arylthio group having 4 to 30 carbon atoms, a phosphoryl group, a dialkylaminocarbonyl group having 2 to 30 carbon atoms, or a monoalkylaminocarbonyl group having 1 to 30 carbon atoms.

2. A nitric oxide donor comprising the fluorofuroxan compound according to claim 1.

3. A method for manufacturing the fluorofuroxan compound represented by general formula (1) according to claim 1, the method comprising a step of reacting a nitrofuroxan compound represented by general formula (3) below with a fluoride salt to substitute a nitro group with a fluoro group:

[Chemical Formula 2]

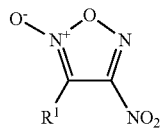

(3)

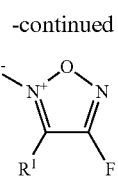

(1)

wherein $R^1$ is the same as $R^1$ defined in claim 1.

4. A method for manufacturing the fluorofuroxan compound represented by general formula (2) according to claim 1, the method comprising a step of isomerizing the fluorofuroxan compound represented by general formula (1) according to claim 1 by irradiation with light:

[Chemical Formula 3]

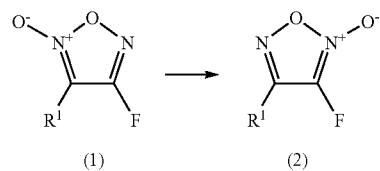

(1)  (2)

wherein $R^1$ is the same as $R^1$ defined in claim 1.

5. The fluorofuroxan compound according to claim 1, wherein $R^1$ represents an alkyl group having 1 to 30 carbon atoms, an alkenyl group having 2 to 30 carbon atoms, an alkynyl group having 2 to 30 carbon atoms, or an aryl group having 4 to 30 carbon atoms.

6. The fluorofuroxan compound according to claim 1, wherein $R^1$ represents an aryl group having 4 to 30 carbon atoms.

* * * * *